(12) United States Patent
Sadler (10) Patent No.: US 10,130,247 B2
(45) Date of Patent: Nov. 20, 2018

(54) CALCULATING LIGHT PROJECTION OBSTRUCTION IN HUMAN VISION ANALYSIS

(75) Inventor: Stephen Sadler, Clarkston, MI (US)

(73) Assignee: OCULAR3D LLC, Clarkston, MI (US)

( * ) Notice: Subject to any disclaimer, the term of this patent is extended or adjusted under 35 U.S.C. 154(b) by 1197 days.

(21) Appl. No.: 12/225,358

(22) PCT Filed: Mar. 20, 2007

(86) PCT No.: PCT/US2007/006907
§ 371 (c)(1),
(2), (4) Date: Sep. 19, 2008

(87) PCT Pub. No.: WO2007/109269
PCT Pub. Date: Sep. 27, 2007

(65) Prior Publication Data
US 2015/0208912 A1      Jul. 30, 2015

Related U.S. Application Data

(60) Provisional application No. 60/784,015, filed on Mar. 20, 2006.

(51) Int. Cl.
*A61B 3/00* (2006.01)
*G06T 15/40* (2011.01)
*G06T 19/00* (2011.01)

(52) U.S. Cl.
CPC ............ *A61B 3/0025* (2013.01); *G06T 15/40* (2013.01); *G06T 19/00* (2013.01)

(58) Field of Classification Search
None
See application file for complete search history.

(56) References Cited

U.S. PATENT DOCUMENTS

| 6,113,643 A | 9/2000 | Weber et al. |
| 6,113,644 A | 9/2000 | Weber et al. |

FOREIGN PATENT DOCUMENTS

| EP | 1 343 119 | 9/2003 |
| GB | 2 333 383 | 7/1997 |

OTHER PUBLICATIONS

Timothy M. Boundy et al., "'Multi Vector' Field of View Design Tool," SAE Technical Paper 2004-01-0380, Mar. 8, 2004, 6 pages without numbering.
Andre et al.; "Legibility of In-Vehicle Displays"; symposium; Dec. 17, 1998; pp. 1-67; Virginia Polytechnic Institute and State University; Blackburg, Virginia.

*Primary Examiner* — G Steven Vanni
(74) *Attorney, Agent, or Firm* — Preston Smirman; Smirman IP Law, PLLC (57) ABSTRACT

The present invention is the integration of formulas, algorithms, databases, and interactive interfaces. The technology results in a user friendly software application that captures, documents, and delivers the results of human vision studies via a secure web server. The present invention is a method for incorporating commercially available software having an Application Program Interface (API) for calculating the amount of vision obstruction for a particular device by producing a rendered image having pixels and designating the pixels in the rendered image to have various colors. Certain types of colors are designated for representing objects in the rendered image to be visible to the user, and other types of colors are designated to represent objects which are obstructed in the rendered image.

9 Claims, 11 Drawing Sheets

CALCULATING LIGHT PROJECTION OBSTRUCTION IN HUMAN VISION ANALYSIS

CROSS-REFERENCE TO RELATED APPLICATIONS

This application is a National Stage of International Application No. PCT/US2007/006907, filed Mar. 20, 2007, which claims the benefit of U.S. Provisional Application No. 60/784,015, filed Mar. 20, 2006.

FIELD OF THE INVENTION

This invention relates to the area of human vision criteria, and the ability for various companies to comply with the government standard for human vision criteria.

BACKGROUND OF THE INVENTION

Various products that require human interaction have to comply with human vision criteria. Human vision criteria are the requirements a product, such as an automobile, must have with regard to a human being able to see the environment surrounding the automobile without obstruction from objects such as a headrest when looking forward, backwards, and on both sides of the vehicle. The various criteria (or vision obstruction requirements) are mandated by the government for all automotive and aerospace companies defined by the Federal Motor Vehicle Safety Standard (FMVSS), the National Highway Traffic Safety Administration (NHTSA), Society of Automotive, Aerospace, and Aeronautical Engineers (SAE), and the like.

Current vision studies do not employ any specific computer software or other quantitative way of ensuring various products comply with the government vision criteria. Rather, typical vision obstruction studies are performed using manual paper-based and physical prototypes which are flawed in that they are time consuming, lack accuracy in that the present methods are visual (giving subjective results), take up massive amounts of space because the paper having the results from testing must kept in filing cabinets for a specified period by government mandate which can be up to 50 years, and the manual studies are not easily accessible.

Accordingly, there exists a need to eliminate the aforementioned problems and improve the accuracy by eliminating the subjectiveness of human vision criteria testing.

SUMMARY OF THE INVENTION

The present invention is the integration of formulas, algorithms, databases, and interactive interfaces. The technology results in a user friendly software application that captures, documents, and delivers the results of human vision studies via a secure web server. The present invention is a method for incorporating commercially available software having an Application Program Interface (API) for calculating the amount of vision obstruction for a particular device by producing an image having pixels and designating the pixels in the image to have various colors. Certain types of colors are designated for representing objects in the image to be in view of the user, and other types of colors are designated to represent objects which are obstructed in the image.

The amount of obstruction of the various objects is tabulated by calculating the percentages of the objects in the image to be in view, and the objects which are obstructed in the image, by dividing the amount of the pixels of each type of color by the total amount of pixels, thereby producing the amount of obstructed objects in the image.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of the preferred embodiment(s) is merely exemplary in nature and is in no way intended to limit the invention, its applications, or uses.

The present invention uses a scheme for creating, cataloging, and running analysis for, but not limited to, vision obscuration studies. The present invention is a multi-vector vision quantification service which incorporates current commercially available existing software (such as Unigraphics or Catia) having an Application Program Interface (API) with the programming software of the present invention. The combination of software is then used to create a series of rendered images which capture the effects of a light projected from predefined eye points with a single color designated for each. These rendered images are then packaged and uploaded to an webserver providing software as a service (SAAS). The present invention may also be used as a stand-alone service, and does not have to be used in combination with client API.

Figure 1:
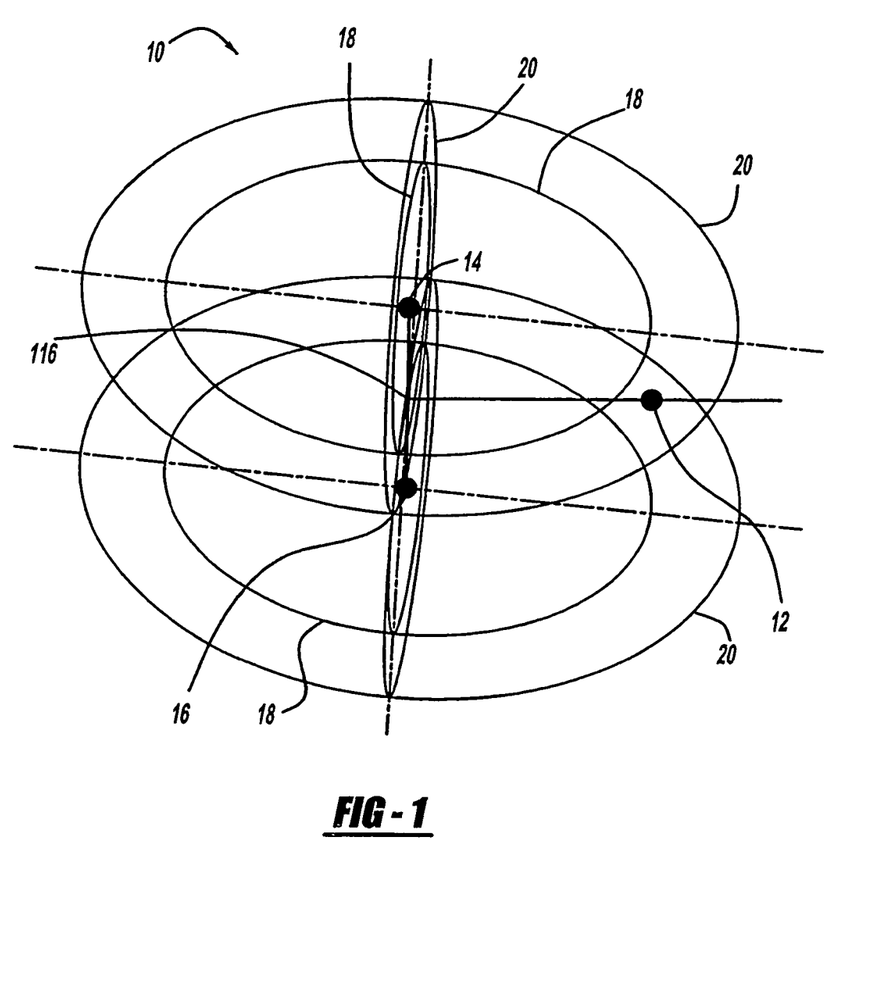
FIG. 1 is a top view of a simulation of the range of motion for a human right eye and left eye used in a human vision analysis system, according to the present invention.

Referring to FIG. 1, a diagram showing several points used in a multi-vector vision quantification service according to the present invention is shown generally at 10. One of the points on the diagram 10 represents a neck pivot point 12, other points represent a right eye 14, and a left eye 16. These points 12, 14, 16 represent the position of the eyes and neck of a human being. Also shown on the diagram 10 are a first set of ellipses 18, and a second set of ellipses 20. The first set of ellipses 18 represent the available range of movement for the ninety-fifth percentile of the human population for the first eye 14 and the second eye 16 when the head of a human being is moved using only the neck. The second set of ellipses 20 represent the range of movement of the human head for the ninety-ninth percentile of the human population for the first eye 14 and the second eye 16 when the head of a human being is moved using only the neck.

Referring to FIGS. 2-5, and FIG. 9, the entire area available that a human being can see from the right eye 14 and left eye 16 of the surrounding environment is represented by a sphere 22 having a center 24, relative to the center position between the right eye 14 and left eye 16. The sphere 22 is three dimensional and has three axes, a first axis 26, or "X-axis," a second axis 28, or "Y-axis," and a third axis 30, or a "Z-axis." Regardless of how the body, neck, or eyes are positioned, a human being can look to the left, right, upward, downward, forward, rearward, or any combination thereof, the sphere 22 will represent the entire viewing area available to the right eye 14 and left eye 16.

Figure 2:
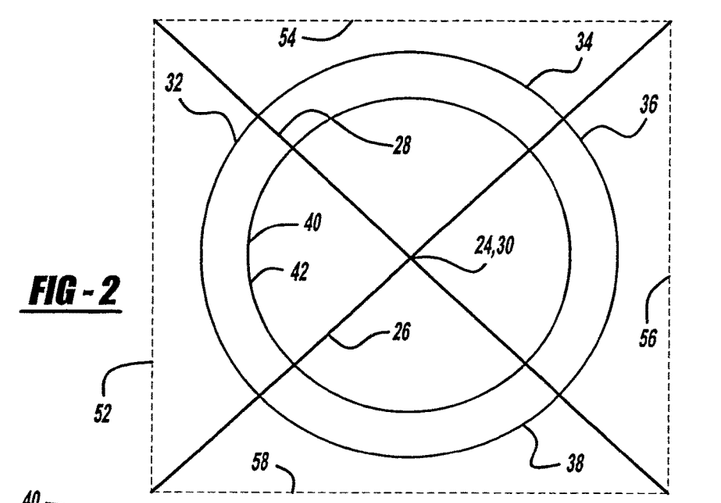
FIG. 2 is a top view of a sphere used a human vision analysis system, according to the present invention.
Figure 3:
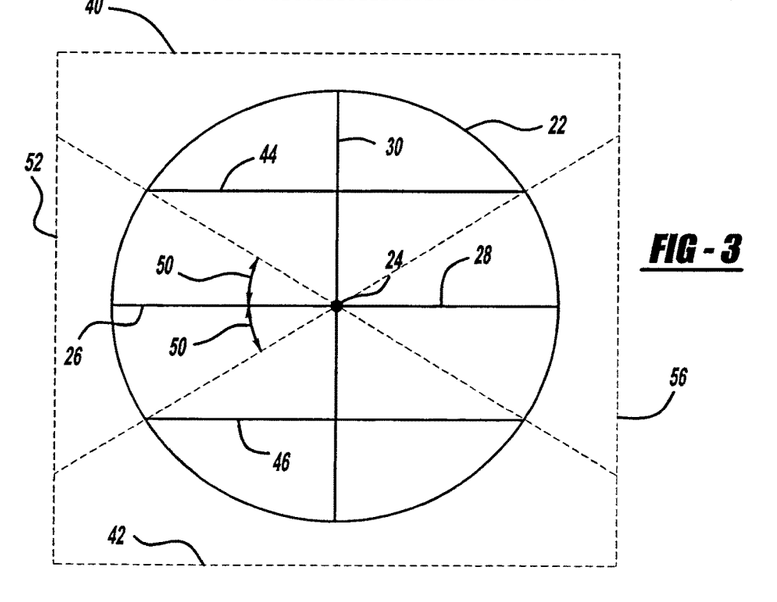
FIG. 3 is a side view of a sphere used a human vision analysis system, according to the present invention.

A steradian (sr) is the standard unit of solid angle measurement in mathematics for spheres. There are $2\pi$ radians in a circle, therefore, there are $4\pi^2$ radians in a sphere. Also, since there are 360° in a circle, one sphere is equal to 360° multiplied by 360°, yielding 129,600 square degrees of theoretical viewing space in a sphere, which applies to the sphere 22 of the present invention. Thus, 129,600 square degrees is equal to $4\pi^2$ steradians. If the sphere 22 is then divided up into equal sections, with section each section having a length of one degree and a width of one degree, each section would have an area of one square degree. One steradian is approximately equal to 3282.8063 square degrees, and one square degree is equal to 0.00030462 steradians. With regard to the application of square degrees to the present invention; one square degree is equal to one Visual Mass Unit (VMU), the function of which will be described later.

Figure 9:
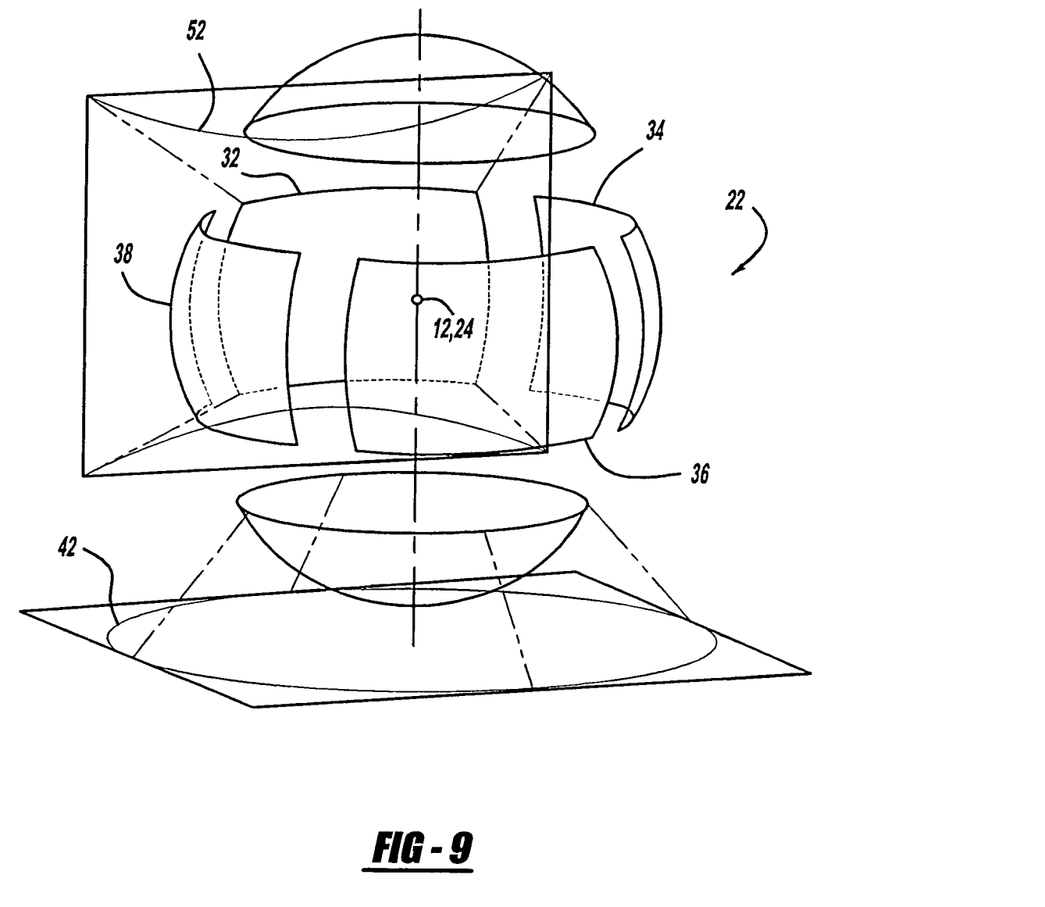
FIG. 9 is an exploded isometric view of a sphere used in a human vision analysis system, according to the present invention.

To perform the analysis according to the present invention, the sphere 22 is broken up into six sections, forming four quadrants of equal size, a first quadrant 32, a second quadrant 34, a third quadrant 36, and a fourth quadrant 38, and two circles of equal size, a first or upper circle 40, and a second or lower circle 42. Each quadrant 32,34,36,38 represents 12.5% of the viewing area available, and each circle 40,42 represents 25% of the viewing area available. The quadrants 32,34,36,38 are created by dividing the sphere 22 once along the first axis 26, and once along the second axis 28 perpendicular to the division of the first axis 26; this creates four quadrants 32,34,36,38 relative to the center 24, one in a forward direction, one in a rearward direction, one in a first side direction, and another in a second side direction. The sphere 22 is then divided along a plane above the center 24 to form a first plane or upper plane 44, and below the center 24 to form a second plane or lower plane 46, with both planes 44,46 being parallel to the first axis 26 and the second axis 28, and equidistant from the center 24. The distance above the center 24 of the sphere 22 where the upper plane 44 is located at a vertical distance 48 opposite of an angle 50 when looking at FIG. 5. The angle 50 is thirty degrees. This process is repeated to obtain the lower plane 46

Figure 4:
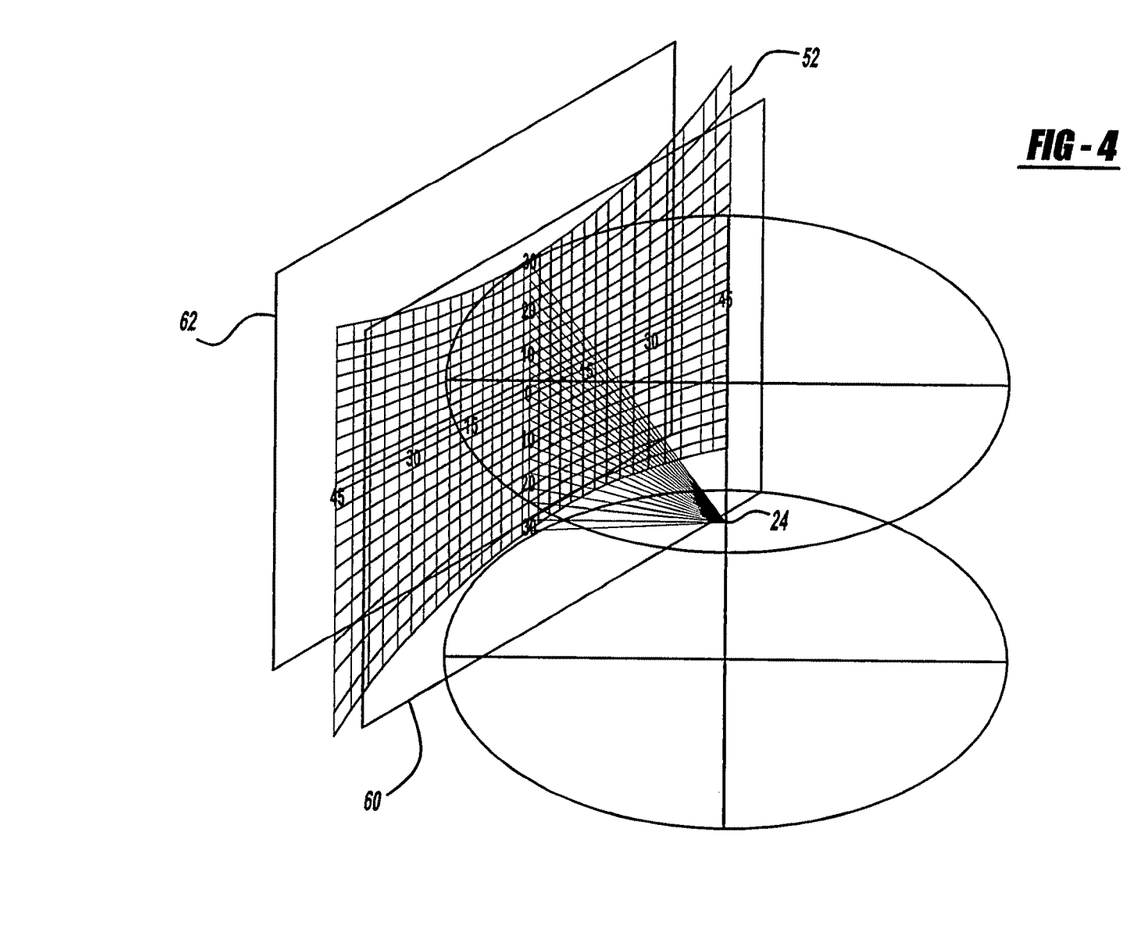
FIG. 4 is an isometric view of a first hyperbola-shaped viewing area with a front clip plane and a back clip plane, used in a human vision analysis system, according to the present invention.
Figure 5:
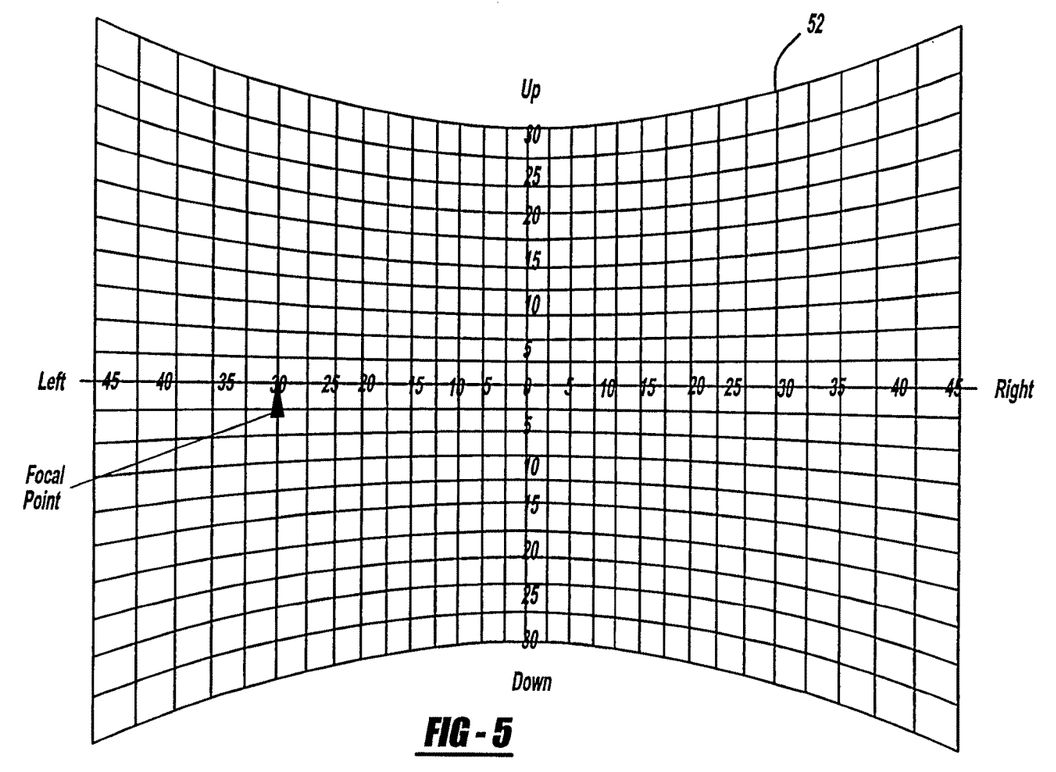
FIG. 5 is a front view of a first hyperbola-shaped viewing area, used in a human vision analysis system, according to the present invention.

Each of the quadrants 32,34,36,38 is then projected onto a flat plane, creating four hyperbola-shaped viewing areas, a first hyperbola-shaped viewing area 52, a second hyperbola-shaped viewing area 54, a third hyperbola-shaped viewing area 56, and a fourth hyperbola-shaped viewing area 58. The four hyperbola-shaped viewing areas 52,54,56,58 along with the upper and lower circles 40,42 together therefore represent the entire viewing area encompassed by the sphere 22 surrounding the center 24. By way of a non-limiting example, the first hyperbola-shaped viewing area 52 is shown in FIGS. 4 and 5, and is similar to the other hyperbola-shaped viewing areas 54,56,58.

The next step in performing the analysis is to simulate the projection of light from the right eye 14 and the left eye 16 onto each of the hyperbola-shaped viewing areas 52,54,56, 58, and the upper and lower circles 40,42 to generate a rendered image of what is seen. The simulation of light projection is from the right eye 14 and the left eye 16. The right eye 14 and left eye 16 are located relative to a single point, shown as a centroid 116. The centroid 116 is located in the middle between the right eye 14 and left eye 16, and is also aligned with the neck pivot point 12. The rendered images projected onto the hyperbola-shaped viewing areas 52,54,56,58 and the upper and lower circles 40,42 are each divided equally into a given number of units, such as pixels seen on a computer screen. Each rendered image is processed individually.

The formation and location of the hyperbola-shaped viewing areas 52,54,56,58 and the upper and lower circles 40,42 is based on the center 24 of the sphere 22. However, the simulation of light projection from the right eye 14 and left eye 16 can vary in relation to the center 24 of the sphere 22. The location of the right eye 14 and left eye 16 can be changed. Each time the location of the right eye 14 and left eye 16 are changed, and simulated light is projected from the right eye 14 and left eye 16 to produce a rendered image, a new "study" is created that can be captured and stored for analysis to determine what can be seen by the right eye 14 and left eye 16. At the beginning to each study, the location of the centroid 116 is chosen, and the location of the right eye 14 and left eye 16 is based on the location of the centroid 116. The location of the neck pivot point 12 is also determined based on the location of the centroid 116. The neck pivot 12 is in the same location as the center 24 of the sphere 22 at the beginning of each study. However, the right eye 14 and left eye 16 can pivot about the neck pivot point 12 after the study begins, allowing for the simulation of light projection through the right eye 14 and left eye 16 to produce different images on the hyperbola-shaped viewing areas 52,54,56,58 and the upper and lower circles 40,42. Each study can have its own simulated environment that can be projected onto the hyperbola-shaped viewing areas 52,54, 56,58 and the upper and lower circles 40,42.

Also, the location of the neck pivot point 12, and therefore the center 24 of the sphere 22, can be changed to also produce other various simulated environments, in addition to the right eye 14 and left eye 16 being able to pivot about the neck pivot point 12. However, the position of each of the hyperbola-shaped viewing areas 52,54,56,58 and the upper and lower circles 40,42 remains constant in relation to the neck pivot point 12 and center 24 of the sphere 22. What varies is the images projected onto the hyperbola-shaped viewing areas 52,54,56,58 and the upper and lower circles 40,42.

The present invention uses various colors and shading for each pixel to demonstrate what can be seen with the right eye 14 individually, the left eye 16 individually, and both the right eye 14 and left eye 16 simultaneously. What can be seen by only the right eye 14 can be represented by one color, such as yellow pixels, what can be seen by only the left eye 16 can be represented by another color, such as blue pixels, and what can be seen by both the right eye 14 and left eye 16 can be represented by white pixels. What cannot be seen can be represented by black pixels. In the example shown in FIG. 10, the colors are represented by various shading, the function of which will be described later.

There are portions of the rendered image which can be partially seen by both the right eye 14 and the left eye 16, these pixels are designated as gray pixels. Each of the gray pixels is then analyzed, if the gray pixels are dark enough (i.e. reach a predetermined threshold), they are designated as black pixels. If the gray pixels are not dark enough, they are analyzed further and matched to predetermined minimum and maximum thresholds for viewing capabilities of the right eye 14, the left eye 16, and viewing capabilities of both the right eye 14 combined with the left eye 16.

The amount of each blue, yellow, white, and black pixels are then calculated; percentages of each color are calculated by dividing the number of pixels of each color with the total number of pixels and multiplying by 100. For example, the total number of blue pixels is divided by the total number of pixels the rendered image has and is divided by 100, yielding a percentage of blue pixels. The value for Sphere Scale (SS), Steradians (SR) Solid Angle Measure, Visual Mass Units (VMU) is obtained by multiplying the SS, SR, VMU scalar factors with the pixel percentage for each color. Once the SS, SR, and VMU totals for each image are reached, the totals for the right eye 14 and left eye 16 individually can be added together to obtain the percentage of what can be seen by the right eye 14, the left eye 16, and the right eye 14 and left eye 16 together can be added together to obtain what can be seen for all the images used in the environment simulated in the study.

Referring to FIG. 4, a front clip plane 60 and a back clip plane 62 are also part of the rendered image on each of the hyperbola-shaped viewing areas 52,54,56,58. The front clip plane 60 and the back clip plane 62 represent the portions of the objects in the rendered image which have been removed, and are not shown in the rendered image projected onto the hyperbola-shaped viewing areas 52,54,56,58. The shadows from the object in the rendered image are still projected in the various colors described above, but the object itself is removed such that the shadows can be seen more easily.

The multi-vector vision quantification service of the present invention can include, without limitation, computer servers, computer networks, data storage devices, optical mediums (CD, DVD, or the like), transmissions of the subject matter across a wide area network, transmissions of the subject matter across a local area network, transmissions of the subject matter from one data storage device to a second data storage device, and wireless transmissions of the subject matter.

Figure 6A:
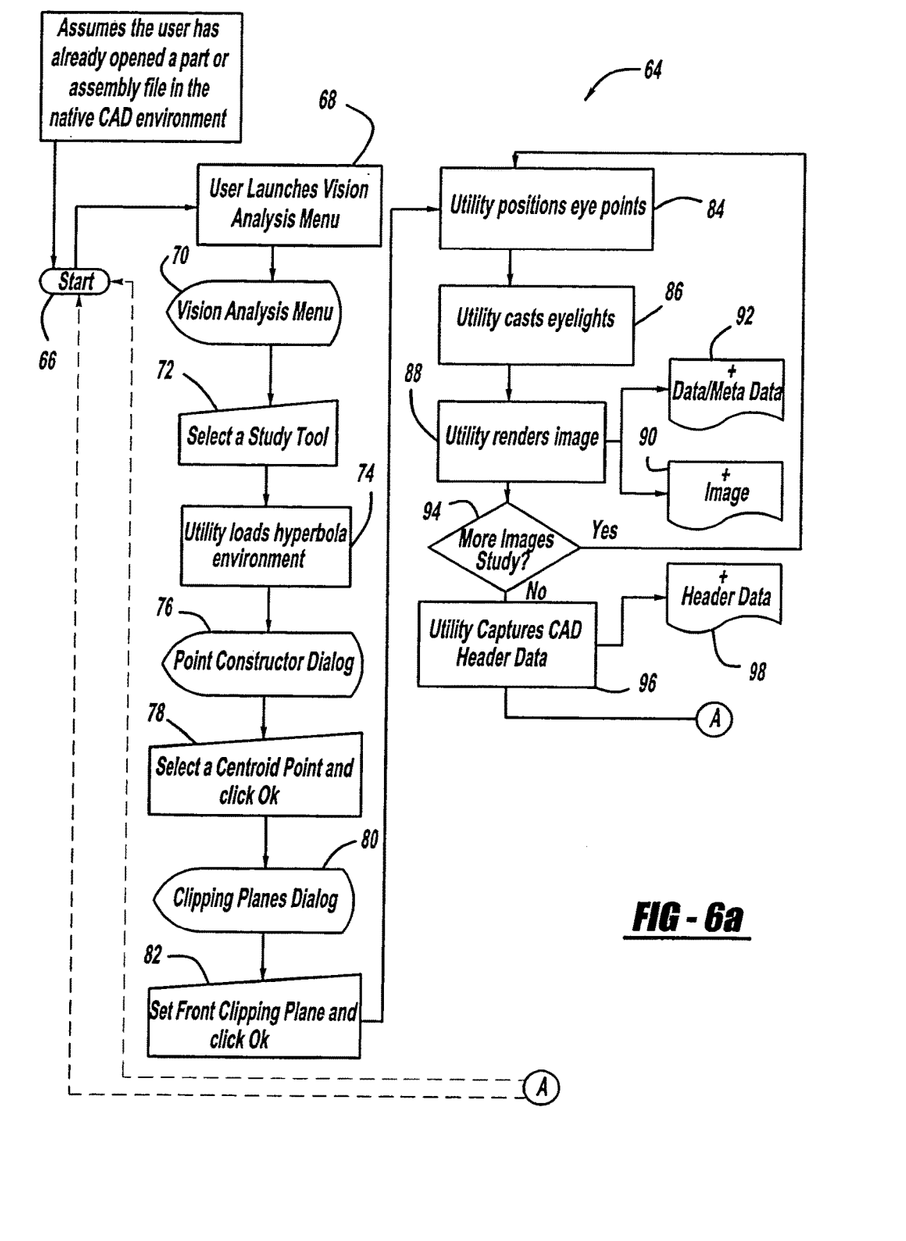
FIG. 6a is first portion of a schematic illustration of a flowchart used in a human vision analysis system, according to the present invention
Figure 6B:
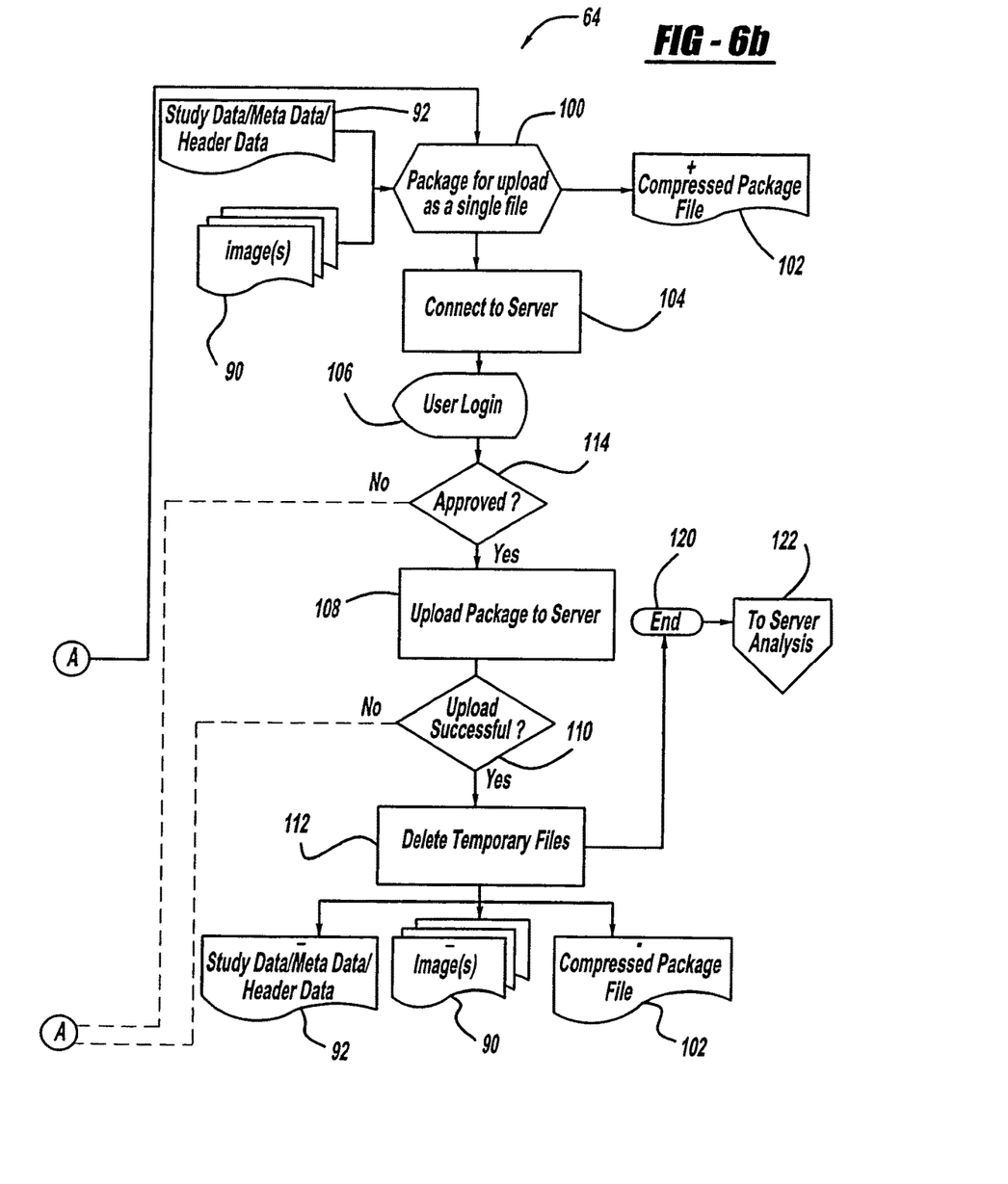
FIG. 6b is a second portion of a schematic illustration of a flowchart used in a human vision analysis system, according to the present invention.

Referring to FIGS. 6a and 6b, there is shown generally at 64 a flowchart illustrating the client utility portion of the processing steps of a multi-vector vision quantification service of the present invention. The course multi-vector vision quantification service of the present invention can be practiced in conjunction with the Internet, World Wide Web, intranets, extranets, electronic media (e.g., CD/DVD-based systems), or the like.

By way of a non-limiting example, a user navigates to the URL of the main Web Site that contains the course development program of the present invention (e.g., with the aid of a Web browser, such as INTERNET EXPLORER, NETSCAPE, or the like). By way of a non-limiting example, the URL http://www.scatemvv.com can be designated as the main Web Site for the multi-vector vision quantification service of the present invention.

Referring again to the flowchart 64, a user will have opened a file that presents the object or objects to be viewed in a Computer Aided Design (CAD) or equivalent design environment. Beginning at a start block 66, the user will launch with the Vision Analysis Menu 68, at this point the user will interface with the Vision Analysis Menu 70 and be prompted to Select A Study Tool 72, which will require manual input by the user. In this step, the user is selecting the environment which will be used in the particular study, such as the interior of an automobile shown in the example in FIG. 10.

Once the user has Selected A Study Tool 72, the hyperbola environment will be loaded, shown as the Utility Loads Hyperbola Environment 74. The hyperbola environment 74 consists of the hyperbola-shaped viewing areas 52,54,56,58, and the upper and lower circles 40,42 described above. Once the hyperbola environment 74 is loaded, the user will interface with the Point Constructor Dialog 76, where the user will be prompted to select a centroid point. The user will then progress to the step where the user will Select A Centroid Point 78. This step 78 involves selecting the location of the centroid 116 (shown in FIGS. 1 and 9). Once the centroid 116 is selected, the user will reach the Clipping Planes Dialog Window 80, and the user will then manually input, and Set The Front and Back Clip Planes 82, where locations of the clip planes 60,62 are set in relation to each of the hyperbola-shaped viewing areas 52,54,56,58. There is a front clip plane 60 and a back clip plane 62 for each of the hyperbola-shaped viewing areas 52,54,56,58 (shown in FIG. 4).

After the clip planes 60,62 are set, the system will position the eye points, shown as block 84. The system will then simulate light being cast from the right eye 14 and left eye 16, shown as block 86. The system will then render an image, shown as block 88. The rendered images produced are the rendered images projected onto the hyperbola-shaped viewing areas 52,54,56,58. These rendered images are stored in files, shown as Image Files 90, and the Data/Meta-Data is also stored in files 92.

A logic gate 94 is reached where the system determines whether more rendered images are required for the study. If more rendered images are required, steps 84, 86, and 88 are repeated. If no more rendered images are necessary, the next step, designated 100, occurs where the CAD header data is captured and stored into a Header Data File 98.

The next step occurs where the system prepares the Image Files 90 and the Data/Meta-Data Files 92 for use with a server. This is shown by block 100, where the Image Files 90 and the Data/Meta-Data Files 92 are combined to produce a Compressed Package File 102. After the Compressed Package File 102 is created, the system will connect to the server, represented by block 104. After this point the user will reach the User Log-in Block 106. Once the user has reached the user log-in block 106, a logic gate 114 is then reached as to whether the log-in is approved. If the log-in is not approved, the user is returned to the start block 66. If the log-in is approved, the system will upload the package to the server, represented by block 108.

After the package is uploaded to the server, another logic gate will be reached represented by block 110, which will determine if the upload was successful. If the upload was not successful, the user returns to the start block 66. If the upload was successful, the system will then perform the Delete Temporary Files step, represented by block 112. In this step, the Image Files 90, the Compressed Package Files 102, and the Data/Meta-Data/Header Data 92 files will be deleted. After the temporary files have been deleted, the next step in the process is moved to the end block 120, and onto the server analysis, represented by block 122.

Figure 7:
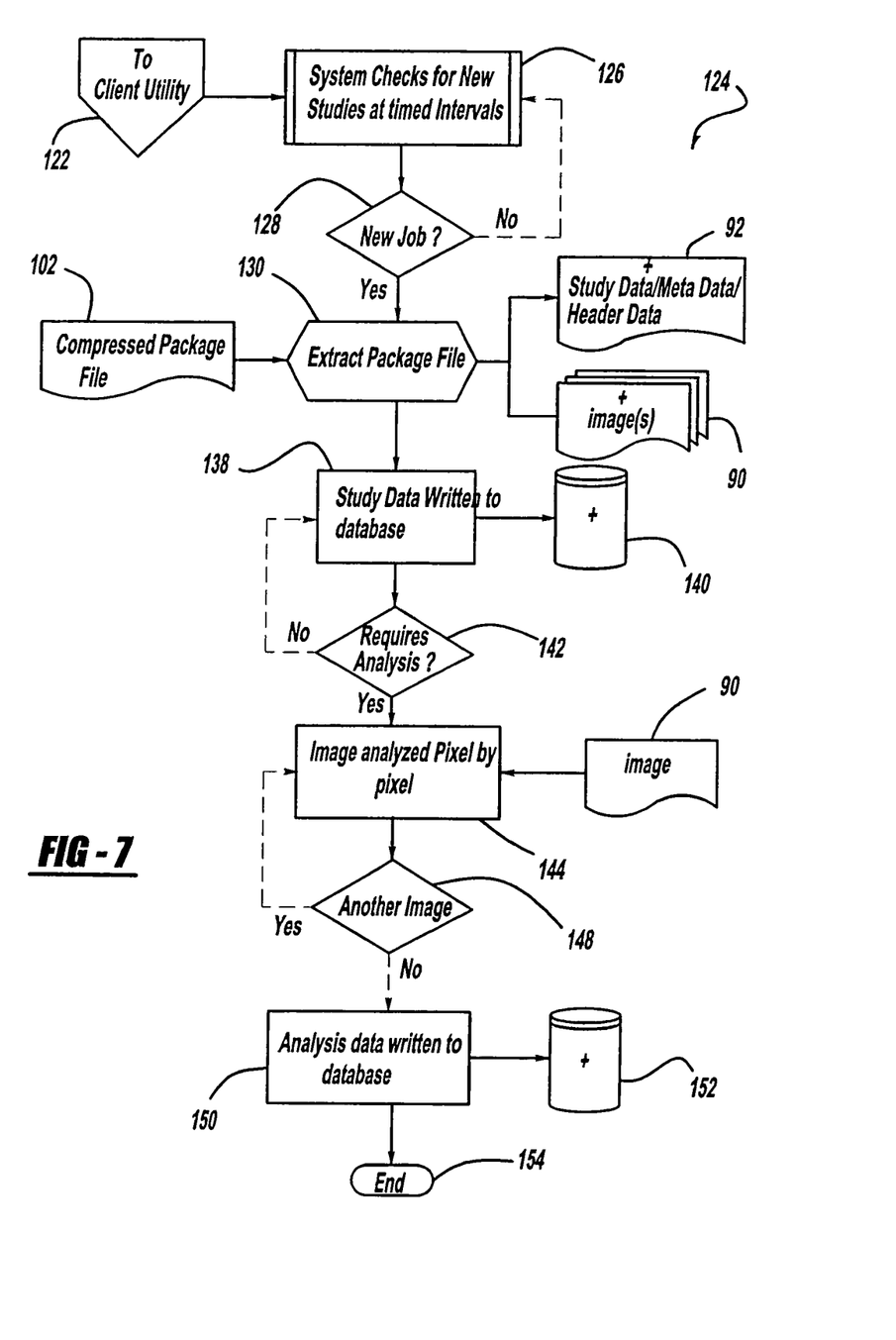
FIG. 7 is a schematic illustration of a flowchart representing the client utility used in a human vision analysis system, according to the present invention.

Once the user has completed the client utility portion, shown by flowchart 64, the user will reach the system server analysis, shown as a flowchart generally at 124 in FIG. 7. The first step in this process is that the present invention checks for new studies at timed intervals, which is represented by block 126 in the flowchart 124. The server has a service which then checks every two minutes for the presence of new, completely uploaded study packages and processes those studies that are ready. Certain studies are "catalog only," which means they are added to the data base and are made available to the person conducting the study via an on-line graphical user interface with no analysis required. Some studies require analysis that is sent to an analysis engine where the following processes are accomplished prior to being made available in the on-line graphical user interface.

The next step is where a logic gate 128 will be reached where it is determined if the study package is a new study package. If the study package is not new, then the step designated as block 126 will be repeated, and the system will check for new studies at the timed intervals. If the job is new then step designated as block 130 is performed, where the Compressed Package File 102 is extracted to open the rendered image files 90 and the Data/Meta-Data/Header Data Files 92. After this step occurs, the data from the particular study being used is written to the data base, represented by block 138. The study is then added to the data base, represented by block 140.

The next step in the analysis is where a decision needs to be made at logic gate 142. The decision that is to be made is whether the study requires analysis. If the study does not require analysis, the step designated as block 138 is then repeated, where the next study is written to the data base. If the study does require analysis, then the next step in the process, represented by block 144, occurs where each rendered image is analyzed pixel by pixel. The system accesses the image files 90, and analyses each image file 90 pixel by pixel. As stated above, each rendered image will have pixels of various colors. Some of the pixels will be blue, others will be yellow, white, or black. Each pixel shown in the rendered image will represent what can be seen by the right eye 14, the left eye 16, neither the right eye 14 or the left eye 16, or the right eye 14 and the left eye 16. The rendered images analyzed at block 144 are the rendered images that are projected onto the hyperbola-shaped viewing areas 52,54, 56,58, and the upper and lower circles 40,42.

After the rendered images are analyzed at block 144, a logic gate 148 is reached where a decision is made as to whether there is another rendered image that needs to be analyzed. If another rendered image needs to be analyzed, the step designated at block 144 is repeated where the rendered image is analyzed. If there is not another rendered image to be analyzed, the next step, designated as block 150, occurs where the analysis data of the study is written to the data base. The analysis data is added to the data base, shown at block 152. After the system server analysis is completed, the system moves to end block 154.

Figure 8:
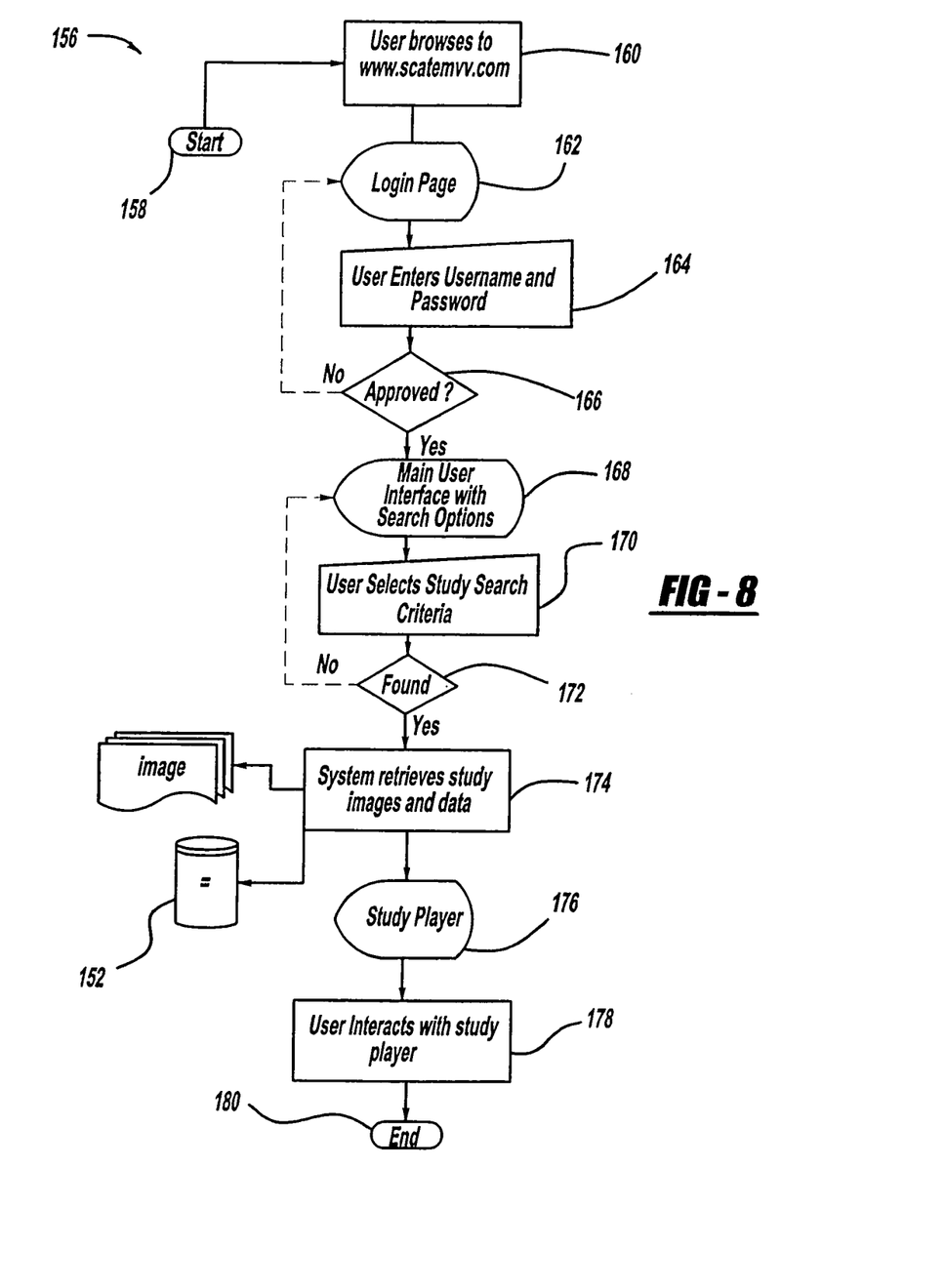
FIG. 8 is a schematic illustration of a flowchart representing the system server analysis used in a human vision analysis system, according to the present invention.

The next step in the process of using the present invention is where the user will perform the system server viewing represented generally as a flowchart at 156, in FIG. 8. In this portion of the process, the user will interact with the server to view the results of each study performed. Beginning at step block 158, the step of accessing the system through the use of a web browser is performed, represented by block 160. A graphical user interface, represented at block 162, is then reached where the user will log-in to the server. The user will then perform the step shown at 164 where the user enters a user name and password at the log-in page 162.

A logic gate is then reached where a decision is made as to whether the user name and password are approved, which is represented by block 166. If the user name and password are not approved, the user is then returned to the log-in page 162. If the user name and password are approved, the main user interface with search options step, represented at block 168, is then performed. At this block, the user will perform the step, represented at block 170, where the user selects the study search criteria. A logic gate 172 is then reached where a decision is made as to whether the study search criteria is found. If the study search criteria is not found, the user will return to the main user interface with search options block 168. If the study search criteria is found, the system will retrieve the study images and data, represented at block 174. At this step the system will retrieve the image files 90 and the study data 152. After the image files 90 and study data 152 are retrieved, the user will move onto the next step of the study player graphical unit user interface 176. The user will then interact with the study player 178. After the user interacts with the study player 178, the use of the program will have been completed, represented at end block 180.

Figure 10:
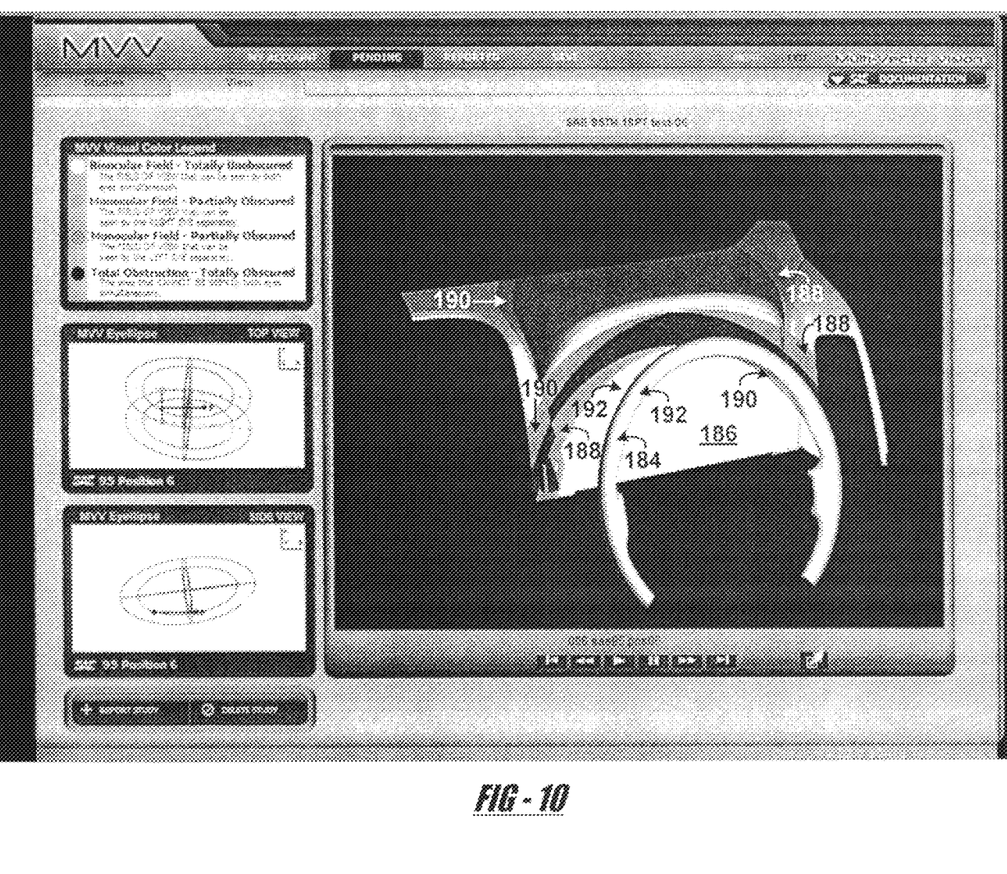
FIG. 10 is an example of a rendered image used in a human vision analysis system, according to the present invention.

By way of a non-limiting example, a rendered image produced in a study using the multi-vector vision quantification service 10 of the present invention is shown generally at 182 in FIG. 10. The image 182 of this example depicts a portion of the interior of an automobile. A steering wheel 184 and a dashboard 186 are shown with portions removed from the image 182 because of the front clip plane 60 and back clip plane 62. In this image 182, the various shadows shown depict what can be seen with both eyes 14,16, and what can be seen with the right eye 14, and left eye 16 individually. The image 182 has a first shadow 188 which represents what can be seen by the right eye 14, a second shadow 190 representing what can be seen by the left eye 16, and a third shadow 192, which represents what can be seen by both eyes 14,16. If the image 182 were in color, the first shadow 188 would be yellow, and the second shadow 190 would be blue.

Figure 11:
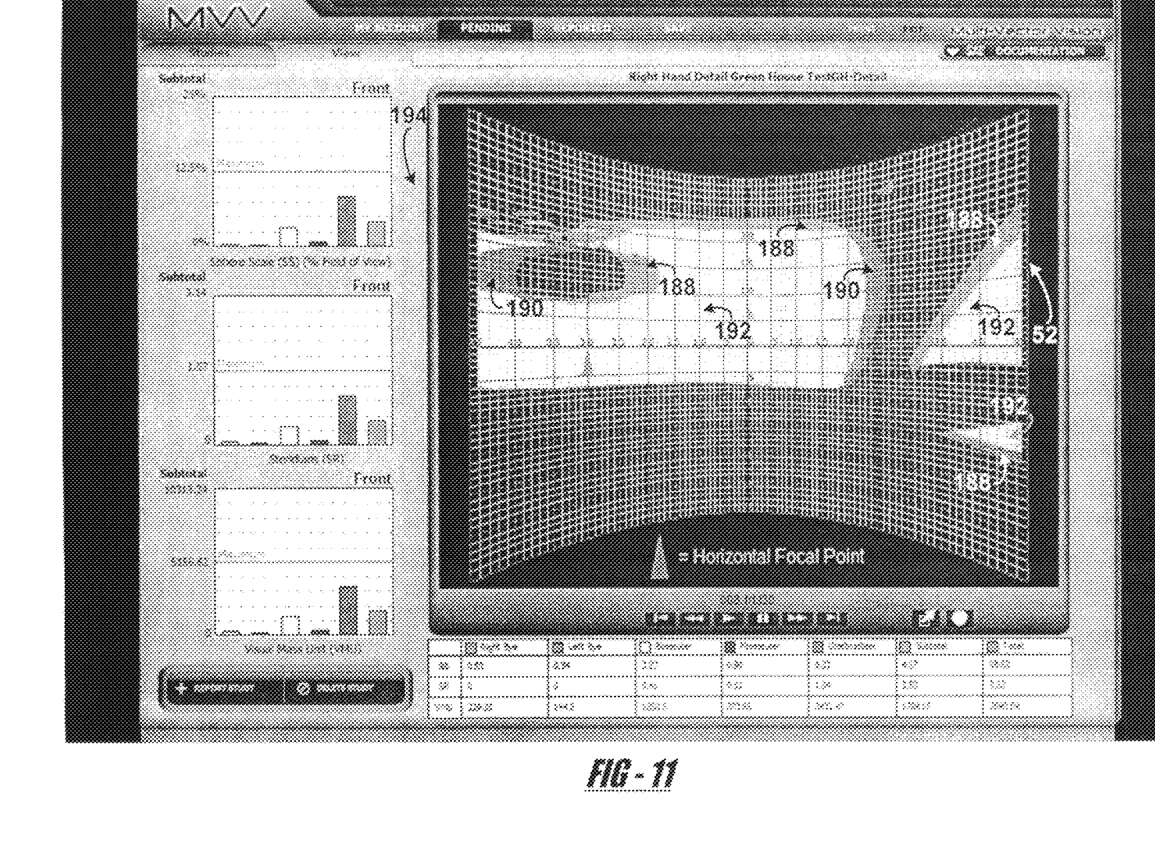
FIG. 11 is a second example of a rendered image projected on a hyperbola-shaped viewing area used in a human vision analysis system, according to the present invention.

Another example of a rendered image produced according to the present invention is shown in FIG. 11. In this example, a rendered image 194 has been projected onto the second hyperbola-shaped viewing area 52. The rendered image 194 is shown, along with the first shadow 188 showing what can be seen by the right eye 14, the second shadow 190 representing what can be seen by the left eye 16, and the third shadow 192, which represents what can be seen by both eyes 14,16. Also, the calculations for SS, SR, and VMU are shown for each eye 14,16 individually, as well as together. Also, the totals for SS, SR, and VMU are shown for the entire environment projected onto the hyperbola-shaped viewing areas 52,54,56,58 and the upper and lower circles 40,42.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for calculating vision obstruction, comprising the steps of:
    providing data representing a physical environment around a human being, portions of the represented physical environment being visible to the human being as a plurality of viewing areas;
    establishing a centroid located between a simulated right eye and a simulated left eye of a human being;
    simulating light projection from the right eye and the left eye of the human being onto at least one of the plurality of viewing areas to produce at least one rendered image comprising a plurality of pixels;
    displaying the at least one rendered image onto at least one of the plurality of viewing areas;
    designating a first set of colors to represent a first plurality of objects which are visible in the at least one rendered image;
    designating a second set of colors to represent a second plurality of objects which are obstructed in the at least one rendered image; and
    determining the numbers of pixels representing the first plurality of objects which are visible and the second plurality of objects which are obstructed by:
        counting the number of pixels, out of a total number of the pixels in at least one of the plurality of viewing areas, to represent what is visible to the right eye only, the left eye only, and the right eye and the left eye;
        designating a first portion of the counted number of pixels to represent each of the first plurality of objects visible to the right eye;
        designating the first portion of the pixels representing each of the first plurality of objects visible to the right eye to have a first color of the first set of colors;
        designating a second portion of the counted number of pixels to represent each of the first plurality of objects visible to the left eye; and
        designating the second portion of the pixels representing each of the first plurality of objects visible to the left eye to have a second color of the first set of colors;
    calculating a percentage of the at least one rendered image visible to the right eye by dividing the first portion of the pixels representing each of the first plurality of objects visible to the right eye by a total number of the pixels; and
    calculating a percentage of the at least one rendered image visible to the left eye by dividing the second portion of the pixels representing each of the first plurality of objects visible to said left eye by the total number of the pixels.

2. The method of calculating vision obstruction of claim 1, further comprising the steps of:
    adding the total number of pixels visible to the right eye for the at least one rendered image displayed onto at least one of the plurality of viewing areas; and
    adding the total number of pixels visible to the left eye for the at least one rendered image displayed onto at least one of the plurality of viewing areas.

3. The method of calculating vision obstruction of claim 1, further comprising the steps of:
    designating a third portion of the counted number of pixels to represent each of the first plurality of objects visible to both of the right eye and the left eye;
    designating the third portion of the pixels representing each of the first plurality of objects visible to both of the right eye and the left eye to have one of a third set of colors;
    designating a fourth portion of the counted number of pixels to represent each of the second plurality of objects obstructed from both of the right eye and the left eye; and
    designating the fourth portion of the pixels representing each of the second plurality of objects obstructed from both of the right eye and the left eye to have one of a fourth set of colors.

4. The method of calculating vision obstruction of claim 3, further comprising the steps of:
    calculating a percentage of the at least one rendered image visible to both of the right eye and the left eye by dividing the third portion of the pixels representing each of the first plurality of objects visible to both of the right eye and the left eye by the total number of pixels; and
    calculating a percentage of the at least one rendered image obstructed from both of the right eye and the left eye by dividing the fourth portion of the pixels representing each of the second plurality of objects obstructed from both of the right eye and the left eye by the total number of pixels.

5. The method of calculating vision obstruction of claim 4, further comprising the steps of:
    calculating a percentage of pixels visible to both of the right eye and the left eye by multiplying the percentage of the at least one rendered image visible to both of the right eye and the left eye by the total number of pixels; and
    calculating a percentage of pixels obstructed from both of the right eye and the left eye by multiplying the percentage of the at least one rendered image obstructed from both of the right eye and the left eye by the total number of pixels.

6. The method of calculating vision obstruction of claim 5, further comprising the step of:
    adding the total number of pixels visible to both of the right eye and the left eye for the at least one rendered image displayed onto at least one of the plurality of viewing areas.

7. The method of calculating vision obstruction of claim 1, wherein the physical environment is a vehicle.

8. The method of calculating vision obstruction of claim 7, wherein the vehicle is an automotive vehicle.

9. The method of calculating vision obstruction of claim 7, wherein the vehicle is an aerospace vehicle.

* * * * *